United States Patent [19]
Sato et al.

[11] Patent Number: 6,046,448
[45] Date of Patent: Apr. 4, 2000

[54] SCANNING NEAR FIELD OPTICAL MICROSCOPE BASED ON THE USE OF POLARIZED LIGHT

[75] Inventors: Katsuaki Sato, Kawasaki; Yasuyuki Mitsuoka; Kunio Nakajima, both of Chiba, all of Japan

[73] Assignee: Seiko Instruments Inc., Japan

[21] Appl. No.: 09/082,508

[22] Filed: May 21, 1998

[30] Foreign Application Priority Data

May 23, 1997 [JP] Japan .................................. 9-134178

[51] Int. Cl.$^7$ ........................................................ H01J 3/14
[52] U.S. Cl. .......................... 250/234; 250/225; 250/306; 354/369
[58] Field of Search ............................ 250/225, 234–236, 250/306, 309, 310, 311; 356/364, 369

[56] References Cited

U.S. PATENT DOCUMENTS

| 5,457,536 | 10/1995 | Kornfield et al. | 356/366 |
| 5,664,036 | 9/1997 | Islam | 250/306 |
| 5,877,891 | 3/1999 | Park et al. | 250/309 |
| 5,960,147 | 9/1999 | Muramatsu et al. | 250/306 |

FOREIGN PATENT DOCUMENTS

| 674200A1 | 9/1995 | European Pat. Off. . |
| WO 9603641 | 2/1996 | WIPO . |

OTHER PUBLICATIONS

Journal of Magnetism and Magnetic Materials, vol. 165, No. 1, Jan., 1997, V. Kottler et al., pp. 398–400, "Dichroic Imaging of Magnetic Domains With a Scanning Near–Field Optical Microscope".

Applied Physics Letters, vol. 65, No. 6, Aug. 1994, T. J. Silva et al., pp. 658–660, "Scanning Near–Field Optical Microscope for the Imaging of Magnetic Domains in Optically Opaque Materials".

*Primary Examiner*—Stephone B. Allen
*Attorney, Agent, or Firm*—Adams & Wilks

[57] ABSTRACT

An optical fiber probe which has a minute opening on the top of a sharpened tip is allowed to get close to a sample, and the probe is moved by a piezo actuator along x- and y-axis directions so that a minute spot beam emanating from the minute opening can scan over the sample. For circular polarization modulation to be incorporated in the process, a beam, before it is incident on the optical fiber probe, is given an optical delay changing at a frequency of p (Hz) by means of a piezo-optical modulator. A minute spot beam emanating from the minute opening passes through the sample to be received after the passage through an analyzer by a light receiving element. The output from the light receiving element is fed to a lock-in amplifier, p- and 2p-components are separated through lock-in rectification, and they are rendered images by a controller.

8 Claims, 5 Drawing Sheets

SCANNING NEAR FIELD OPTICAL MICROSCOPE BASED ON THE USE OF POLARIZED LIGHT

BACKGROUND OF THE INVENTION

This invention relates to a measuring apparatus which measures the polarizing activity and the distribution thereof of a test substance with a high resolution, by detecting a beam which has interacted with a tiny area of substance at the tip of probe, and by utilizing the polarization characteristics the beam presents.

It becomes important to observe, for various test samples, the distribution of their optical activities (circular dichroism and optical rotation) at very tiny areas, and to obtain quantitative evaluations of those optical activities. Such optical activities include natural optical activities, electro-optical activities, magneto-optical activities, and piezo-optical activities, and with the recent technical advance in the field of memories having a gigantic capacity such as a hard disk, opto-magnetic disk, etc., a demand for the equipment allowing a precise observation and measurement of magneto-optical effects becomes rapidly intense.

For example, to observe the distribution of magneto-optic effects as one aspect of such optical activities with a high precision requires to observe magnetic sectors and barriers, and the well-known method used for this purpose includes polarized light microscopy, Lorenz transmission electronmicroscopy, spin-polarized scanning electronmicroscopy, and magnetic force microscopy. A recent article reports an observation of the magnetic barriers of a vertically magnetized membrane by the use of a scanning near field optical microscope (APPLIED OPTICS, Vol. 31, No. 22, 1992, p. 4563, E. Betzig et al.).

Here a scanning near field optical microscope will be briefly sketched. A widely available method consists of sharpening an optic fiber or a beam transmitting body, and preparing a minute opening at its tip having a diameter equal to or less than the wavelength of beam. By the same method with which a conventional scanning atomic force microscope or a scanning tunnel microscope adjusts the distance between a cantilever and a sample, the minute opening is placed so close to the surface of a sample that the distance in between is equal to or less than the wavelength of beam. By introducing, while maintaining above state, a beam into the optic fiber with such minute opening, radiating a tiny area of a sample with the beam emanating from the minute opening, and scanning the beam over the sample in a two-dimensional plane, a microscope can achieve a high resolution microscopy in accordance with the size of minute opening. In the example mentioned earlier where a scanning near field optical microscope was used for the observation of magnetic barriers, a linearly polarized beam emanating from a minute opening is allowed to radiate a sample, and the beam transmitting through the sample is received by an analyzer (cross-Nichol method).

On the other hand, the method by which to quantitatively determine the circular dichroism or optical rotation of a sample, for example, on the basis of magneto-optical effects (methods dependent on other optical activities works on the essentially same principle) is described in detail in "Light and magnetism" published by Asakura Publishing Co. (written by Sato, K.). The optical rotation due to magnetism can be determined by perpendicularly intersecting polarizers (cross-Nichol method), Faraday-cell method, and a rotational analyzer. The use of a quarter-wave plate will allow the measurement of the circular dichroism of sample. Further, modulation of a circularly polarized beam (circular polarization modulation) will enable the measurement of both the magneto-optical rotation and magneto-optical circular dichroism with a high sensitivity.

Here, circular polarization modulation will be briefly sketched with reference to FIG. 2. A linearly polarized beam having passed through a linear polarizer 101 is given, by a piezo-optical modulator 102 working on birefringence, an optical delay which changes at a frequency of p (Hz). Then, the same beam, after having been reflected from or passed through a sample 103 (the beam is reflected from a sample in FIG. 2), is allowed to pass through an analyzer 104 to reach a light receiving element 105 for registration. From p (Hz) component and 2p (Hz) component of the beam having passed through the analyzer 104, it is possible to determine the circular dichroism and optical rotation the beam has undergone, respectively.

The principle underlying circular polarization modulation will be described by equations. For brevity, the direction along which a beam transmits is supposed to coincide with z-axis. Let's assume that in FIG. 2 the linear polarizer 101 has an angle of 45° with respect to x-axis. The electric field $E_1$ of the beam having passed through the linear polarizer 101 can be expressed by:

$$E_1 (i+j) \qquad (1)$$

given that i and j are the unit vectors of x- and y-axes respectively.

Given that there is a delay of $\delta$ between x- and y-components of the electric field $E_2$ of the beam which has passed through the piezo-optical modulator 102, $$E_2 \{i+\exp(i\delta)j\} \qquad (2).$$

Assumed that the unit vectors of right- and left-circularly polarized beams are expressed by following equations respectively:

$$r=(i+ij)/2^{1/2}$$

$$l=(i-ij)/2^{1/2},$$

then, E2 can be expressed by the following equation:

$$E2 \{(1-i.\exp(i\delta))r+(1+i.\exp(i\delta))l\} \qquad (3)$$

Suppose that the complexly expressed amplitude reflections of right- and left-circulatory polarized beams are expressed by r+exp(iθ+) and r−exp(iθ−) respectively, then the electric field $E_3$ of reflected beam can be expressed by:

$$E_3 ((1-i.\exp(i\delta))r+\exp(i\theta+)r+(1+i.\exp(i\delta))r.\exp(i\theta-)l\} \qquad (4).$$

The intensity I of the beam emanating from the analyzer having an angle of $\phi$ with respect to x-axis is expressed by:

$$I\{R+(\Delta R/2) \sin \delta + R \sin (\Delta\theta+2\phi) \cos \delta\} \qquad (5)$$

where $R=(r+2+r-2)/2$ $\Delta R=r+2-r-2$ $$\Delta\theta=\theta+-\theta-=-2\theta_k$$
$$\Delta R/R=4\eta_k$$

and where $\theta_k$ represents a Kerr's rotation angle and $\eta_k$ a Kerr's ellipticity. Assumed that $\phi=0$, and $\Delta\theta$ is sufficiently small, $\delta\sim\sin 2\pi pt$. Then, the equation can be resolved by the use of Bessel function into:

$$I\sim I(0)+I(p)\sin 2\pi pt+I(2p)\cos 4\pi pt+ \qquad (6).$$

In this equation, I(o), I(p), and I(2p) represent factors respectively containing 0th-order, 1st-order and 2nd order Bessel functions, and $$I(p)\eta_k, I(2p)\theta_k. \qquad (7)$$

Therefore, p(Hz) component gives the Kerr's ellipticity and 2p(Hz) gives the Kerr's rotation angle. For details, see the above-described "Light and magnetism."

The above-described various methods employed for the observation of minute magnetic sectors have a number of problems as will be described later. For example, polarized light microscopy, operating in the same manner as conventional optical microscopy, has its resolution restricted by the diffraction limit of a beam used, and only achieves a resolution that allows distinguishing the width of about half the wavelength of beam used. Further, as it depends on the cross-Nichols method for detecting the optical activities of a sample, its detection sensitivity is low. Lorenz transmission electronmicroscopy has a resolution sufficiently high to distinguish about 10 nm intervals, but it is only applied to a thinly sectioned sample. Spin-polarized scanning electronmicroscopy has a problem in that it requires a large cost for installment. Magnetic force microscopy has a considerably high resolution that allows discrimination of several tens nm intervals, but it can be scarcely applied for the quantitative determination of the magnitude of a magnetic field or magnetization. Scanning near field optical microscope has its resolution determined principally by the diameter of opening of the probe, and has a considerably high resolution. The conventional minute spot scanning microscopy, however, usually depends, for the detection of optical activities of a sample, on the cross Nichols method, and presents following problems. It allows only a low sensitivity. Notwithstanding that the closer the minute spot beam emanating from a minute opening is to a linearly polarized beam, the higher the detection sensitivity, the minute spot beam emanating from a minute opening is usually elliptically polarized. This may form another cause for a lowered sensitivity.

Among the apparatuses for quantifying various magneto-optical effects, there are some that allow the very sensitive quantification of a rotation angle through modulation, for example, by the use of a rotating analyzer. This method, however, can not be applied to a tiny area exceeding the typical level handled by a conventional optical microscope.

As illustrated above by referring to the microscopic observation of magneto-optical effects as an example, the conventional methods whereby the distribution and quantification of optical activities of a sample have been obtained have more or less defects to be corrected, although some are advantageous in sensitivity, resolution and tolerance of sample handling, and others are advantageous in cost. What is mentioned above applies to the measurement not only of magneto-optical effects but also of optical activities at large. In view of this the object of the present invention is to provide an apparatus with which it is possible to observe/measure the optical activities of a sample with a high resolution and sensitivity, at a low cost, quantitatively, and without imposing any restrictions on the handling of sample.

SUMMARY OF THE INVENTION

It is an object of the present invention to provide a scanning near field optical microscope based on polarized light which requires only a low cost for production because of its being based on the constitution of scanning atomic force microscopy, and allows observation of a sample without imposing any restrictions on the preparation thereof.

It is another object of the present invention to provide a scanning near field optical microscope where the size of a beam to radiate a sample or emanating from a sample is determined by the size of tip according to the principle underlying scanning near field optical microscope, and thus it allows the observation of a sample with a very high resolution without being affected by a diffraction limit.

It is another object of the present invention to provide a scanning near field optical microscope which becomes possible to achieve a highly sensitive circularly polarized modulation by giving a periodically changing optical delay to a beam.

It is a further object of the present invention to provide a scanning near field optical microscope where it is possible to reduce the changes in polarization state due to external disturbing sources when the probe consists of a light transmitting body made of a material having a smaller photo-elasticity coefficient, and it can minimize the adverse effects due to stresses developed as a result of bending when the same material is applied for the preparation of a probe with a hook-like bent.

DETAILED DESCRIPTION OF THE PREFERRED EMBODIMENTS

Figure 1:
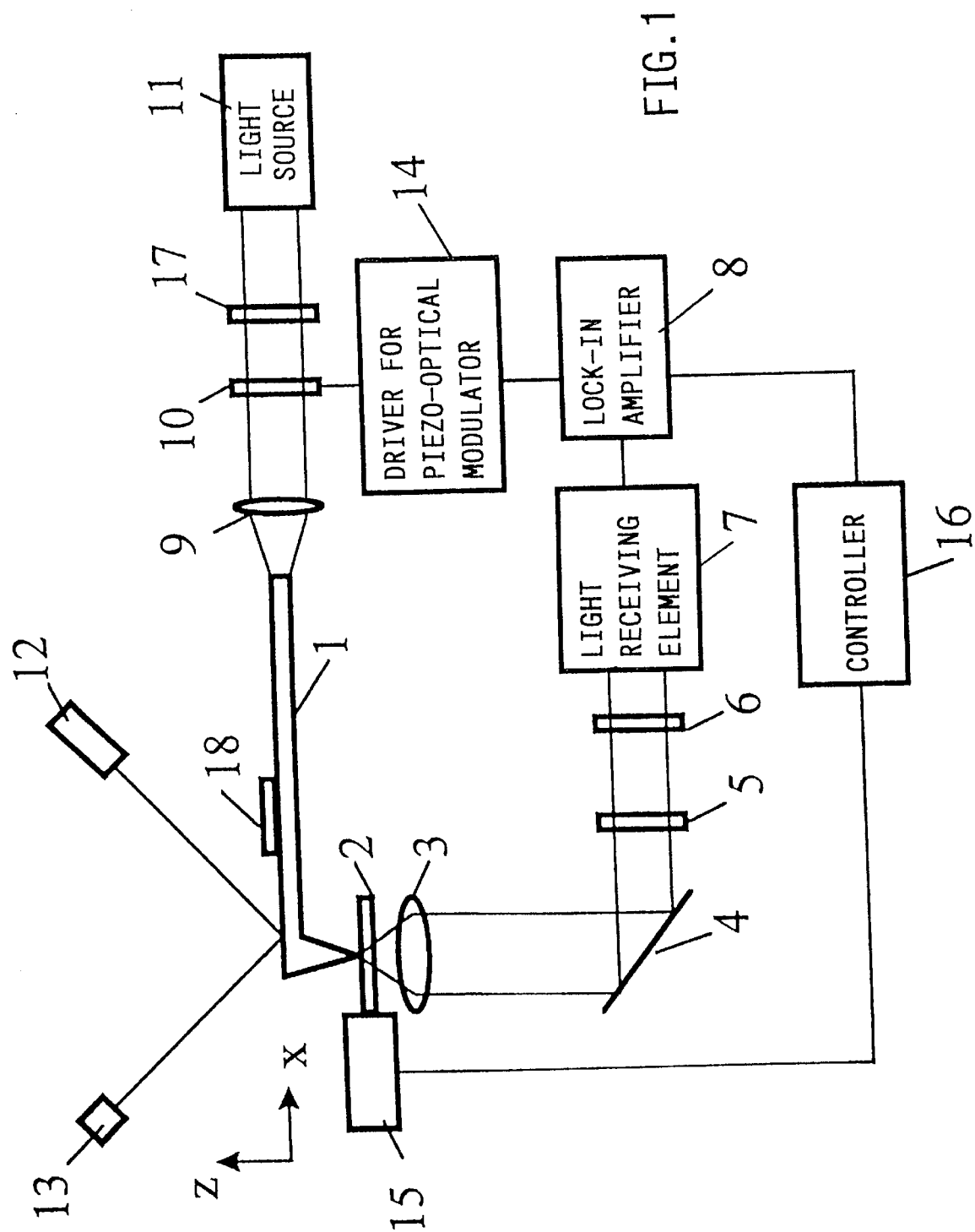
FIG. 1 is an explanatory view showing the constitution of Example 1 of a scanning near field optical microscope based on polarized light according to this invention.
Figure 2:
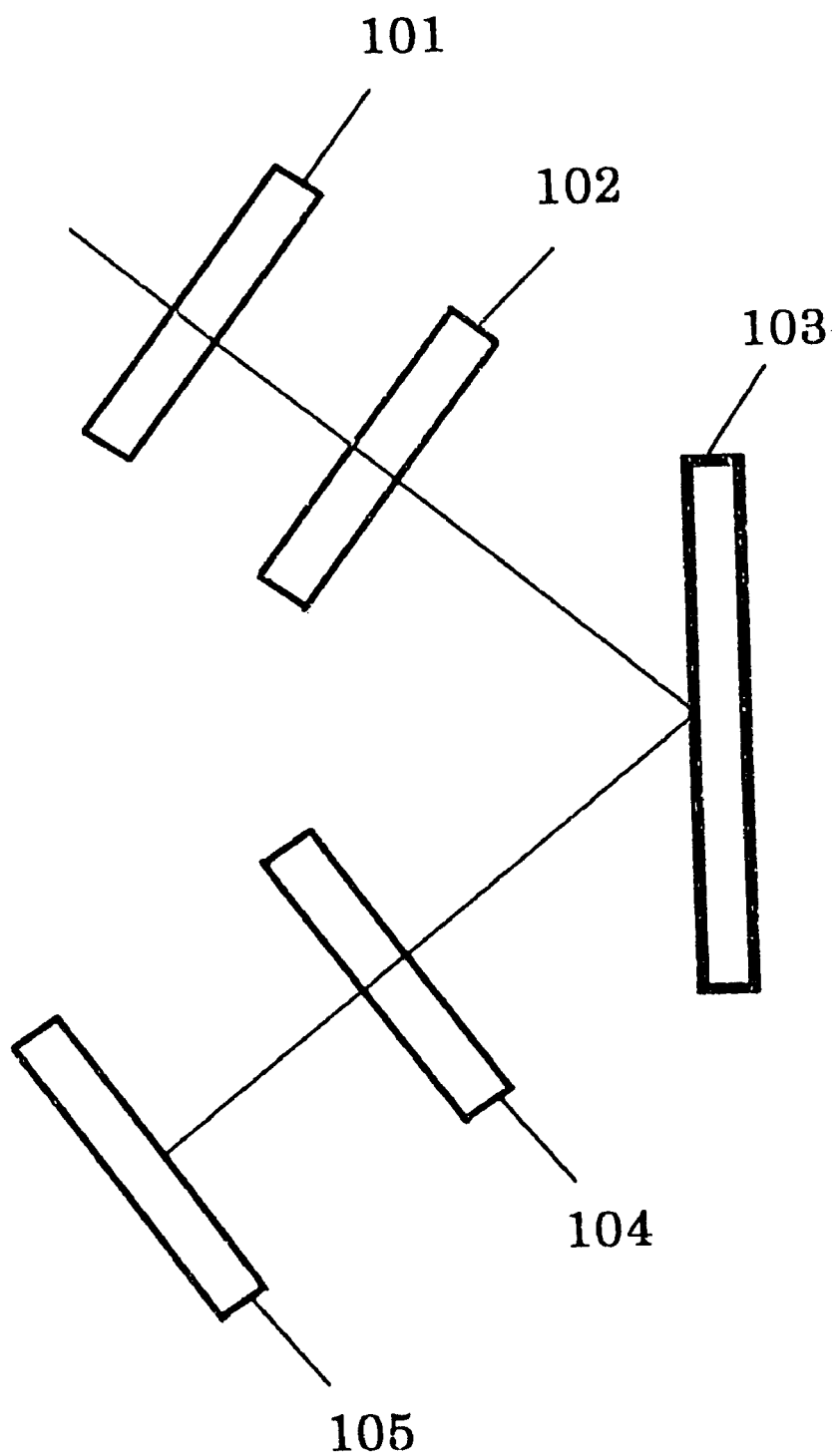
FIG. 2 is an explanatory view showing the constitution of elements necessary for a conventional method for measuring magneto-optical effects based on circularly polarization modulation.

To solve the above-described problem, this invention comprises:
 a light source;
 a probe having a sharpened tip;
 a means which maintains the tip so close to the surface of a sample that the interval therebetween is kept within an action distance which allows an inter-atomic interaction or interactions by way of other elements to be present between the tip and the surface;
 a means which obtains a polarized beam carrying the data of optical activities of a tiny area of the sample or of a medium, by allowing a beam emanating from the source to interact with the sample surface at the tip;
 a light receiving means which receives the polarized beam;

a modulating means which is inserted on a light path between the source and the light receiving means, and gives an optical delay changing at a regular cycle; and a rectifying means which removes, from the output delivered by the light receiving means, components having frequencies as certain integer times high as that of the modulation frequency given by the modulating means. Further, the probe is allowed to have a light transmitting body.

The means which maintains the tip so close to the surface of a sample that the interval therebetween is kept within an action distance which allows an inter-atomic interaction or interactions by way of other elements further comprises:

a moving means which alters the distance between the tip and the surface;

a distance determining means which determines the distance between the tip and the surface; and a control means which maintains the distance between the tip and the surface constant based on a signal delivered by the distance determining means.

The distance determining means still further comprises:

a vibrating means which vibrates the tip and the surface relative to each other in a horizontal or vertical direction; and a displacement detecting means which detects the displacement of the tip.

The modulating means which is inserted on a light path between the source and the light receiving means, and gives an optical delay changing at a regular cycle acts as a means to generate a periodically changing stress in the light transmitting body.

The present invention further comprises:

a light source;

a probe having a sharpened tip and a light transmitting body;

a means which maintains the tip so close to the surface of a sample that the interval therebetween is kept within an action distance which allows an inter-atomic interaction or interactions by way of other elements to be present between the tip and the surface;

a means which obtains a polarized beam carrying the data of optical activities of a tiny area of the sample or of a medium, by allowing a beam emanating from the source to interact with the sample surface at the tip; and a light receiving means which receives the polarized beam, wherein:

the material constituting the light transmitting body has a photo-elasticity coefficient of $10 \times 10^{-6}$ [$mm^2 \cdot N-1$] or less.

The material constituting the light transmitting body includes quartz glass containing lead oxide.

Preferred embodiments of this invention will be described below with reference to attached figures.

(1) EXAMPLE 1

FIG. 1 illustrates the constitution of Example 1 of this invention. The basic constitution is the same with that of a conventional scanning near field optical microscope. The figure shows an apparatus which incorporates an optic fiber probe which is produced after an optic fiber acting as a light transmitting body has a minute opening prepared at its tip, wherein a minute spot beam emanating from the minute opening radiates a sample (illumination mode) and the beam after passing through the sample is registered (transmission type). Description will be given with reference to this example.

Firstly, a conventional minute spot scanning microscopy will be described with regard to its constitution and operation. A light source 11 to produce a gas laser, solid compound-based laser, or semiconductor-based laser generates a light flux, which passes through a polarization adjusting element 17 consisting of a wavelength plate, and a piezo-optical modulator 10, to be incident, through the intervention of a fiber coupler 9, on the input end of optic fiber probe 1. The optic fiber probe 1 is usually made of a single mode fiber, and its other end has its sharpened tip whose circumference is coated by a film composed of a metal like gold or aluminum, such that the tip has a minute opening whose diameter is equal to or less than the wavelength of the beam. The beam incident on the input end of optical fiber probe 1 emanates from the minute opening as a minute spot beam. The optic fiber may be made of a multi-mode fiber or a single hollow fiber, instead of a single mode fiber. Further, the optical fiber probe 1 has a part close to the tip bent like a letter L, and is attached on the surface of a piezo-electric element such as a bimorph or a quartz vibrator. It is possible to operate the apparatus in an AFM mode, or a dynamic mode often used in conjunction with scanning atomic force microscopy (AFM), by vibrating the optical fiber probe 1 vertically with respect to a sample by means of the piezo-electric element 18.

A sample 2 is placed on a piezo actuator 15 which can move along x-, y- and z-axis directions, and a controller 16 controls the movement of piezo actuator 15. The controller, while maintaining constant the distance between the sample 2 and the tip of optical fiber probe 1, scans the beam over the sample 2 in x- and y-axis directions using piezo actuator 15. In this example, a method based on a device generally called an optical lever is used for determining the distance between the sample 2 and the tip of optical fiber probe 1. This method consists of converging a beam emanating from a laser source 12 onto the surface of a mirror placed close to the tip of optical fiber probe 1, of receiving the reflected beam with a bisected light receiving element 13, and of determining the difference between the intensities of beams received by respective bisected segments, thereby to monitor the vibration state (frequency, amplitude and phase of the vibration) of optical fiber probe 1. For example, when the optical fiber probe 1 comes close to the sample 2, its vibration state undergoes a change in the presence of forces resulting from inter-atomic interactions. Therefore, by adjusting the movement of piezo actuator 15 along z-axis direction in such a way as to allow the optical fiber probe 1 to make a vibration with a constant amplitude, it is possible to maintain constant the distance between the surface of sample 2 and the tip of optical fiber probe. Thus, while maintaining constant the distance between the sample 2 and the tip of optical fiber probe 1, it is possible, by scanning the beam over the sample by moving the piezo actuator 15 in x- and y-axis directions, and by monitoring how much the piezo actuator 15 moves along z-axis direction, to obtain the image of surface texture of sample 2.

As the tip of optical fiber probe 1 is positioned close to the surface of sample 2, the minute spot beam emanating from the minute opening transmits through the sample 2, is converged by a converging lens 3, has its path bent by a mirror 4, and passes through an analyzer 5 and filter 6 to be received by a light receiving element 7. The filter 6 placed in front of the light receiving element 7 is to cut off the laser beam 12 which acts as one arm of the optical lever.

As the light source 11 usually consists of a laser source based on a gas or solid molecule, it often happens that a linearly polarized beam impinges on the optical fiber probe 1. But, the optical fiber probe 1 generally contains elements which may resolve the polarization state or retards the phase, of an incident beam, and thus the minute spot beam emanating from the minute opening often suffers a degraded polarization or becomes an elliptically polarized beam, notwithstanding that the incident light is a linearly polarized beam. When such polarized beam is radiated upon the sample 2, and its polarization state is monitored by a cross-Nichols method, the overall sensitivity will become low. To avoid such inconvenience, it is necessary to insert a wavelength plate or compensation plate, that is, an agent to cause an appropriate retardation, on the incident path of optical fiber probe 1, thereby to adjust the polarization state of incident light. Through this procedure it is possible to obtain a minute spot beam with a practically linear polarization.

In spite of above fact, this invention adopts circular polarization modulation dependent on a cross-Nichols method which is principally very sensitive. The method adopted in this example whereby an optical delay is given to a minute spot beam emanating from the minute opening of optical fiber probe 1 in accordance with a modulation frequency of p (Hz) depends on the use of a piezo-optical modulator (PEM) 10 working on birefringence which incorporates an optically active crystal such as quartz or the like. A driver 14 to drive PEM not only activates the piezo-optical modulator 10 but delivers a reference signal with respect to which a lock-in amplifier 8 performs a lock-in rectification. A light flux emanating from the light source 11 passes through the piezo-optical modulator 10 to be given an optical delay there, and is incident through the intervention of fiber coupler 9 on the input end of optical fiber probe 1.

Detection of optical activities using a modulated circularly polarized beam is so sensitive that, as long as any optical delay is given at all to a minute spot beam by means of an external modulating means, it is possible to detect optical activities. What should be noted here is that as long as the piezo-optical modulator 10 incorporates an optically active crystal, the crystal axis has to be taken into account. Namely, modulation efficiency will be higher if an incident polarized beam is adjusted according to the angle the beam forms with the axis of crystal. Thus, the polarized state of an incident beam is adjusted by means of a polarization adjusting element 17 placed on the input side of the piezo-optical modulator 10. Needless to say, the polarization adjusting element 17 may be so constituted as to allow an incident beam to pass through a half wavelength plate capable of rotating the beam, or to allow an incident beam pass through a quarter wavelength plate to convert it into a circularly polarized beam, and then to permit a specific component thereof, say, a linearly polarized beam to exit therefrom. This example uses a piezo-optical modulator 10 incorporating an optically active crystal, but any other modulator can be used with the same profit as long as it can give a periodic optical delay to an incident beam.

Placement of the mirror 4 in front of the analyzer 5 is undesirable because the mirror may add an extra polarization characteristic, and ideally the light path should not be bent. However, for a beam converged by the converging lens 4 to be guided to the light receiving element 7, it is necessary with a conventional transmission type scanning near field optical microscope to bend the light path by means of the mirror 4 for the convenience of designing. The mirror incorporates a dichroic mirror instead of a conventional vapor-deposited aluminum mirror, thereby to lessen the difference in reflection of p- and s-polarized beams. Through this procedure it becomes possible to ignore the polarization characteristic given by the mirror 4.

By virtue of an apparatus having above constitution, a minute spot beam emanating from the minute opening interacts with the surface of sample 2, is converted, through that interaction, into a transmissive beam, passes through the sample 2 being given, during passage, optical activities including circular dichroism and optical rotation, and passes through the analyzer 5 to be incident on the light receiving element 7 so that it may be registered there. This signal is rectified by the lock-in amplifier 8 which uses the reference signal (has a frequency of p) delivered by the PEM driver 14 for rectification, and the rectified output is fed to the controller 16. When 2p component is submitted to lock-in rectification, it gives an optical rotation, and when p component is submitted to lock-in rectification, it gives a circular dichroism. Thus, when these signals are submitted to the controller 16 to be converted into images in synchrony with the scanning movement of piezo actuator 15 as in a conventional scanning near field optical microscope, they will visualize the distribution of optical activities of sample. Incidentally, if only p component is required, the analyzer 5 placed in front of the light receiving element 7 may be omitted.

Further, when not only the distribution of optical activities but also the absolute quantities of those activities are desired, the ratio of p component to the direct current component will give the ellipticity and the ratio of 2p component to the direct current component will give the optical rotation. For the latter purpose it is not necessary to move the piezo actuator 15 so that the beam can scan over the sample along x- and y-axis directions, but to adjust the piezo actuator 15 such that a desired spot of sample 2 is placed close to the optical fiber probe 1 for measurement. By this process it is possible to quantitatively determine the optical activities of a very tiny area of sample as with a conventional method based on the modulation of a circularly polarized beam.

Assumed that the optical fiber probe 1 gives an optical delay of $\pi/2$ as a result of mechanical stresses as does a quarter wavelength plate, the electric field $E_2$ of a beam as described by equation (2) in the "Description of the Related Art" comes to be expressed by the following equation because of an optical delay given by the optical fiber probe 1.

$$Ex\{i+i.exp(i\delta)j\} \qquad (2')$$

As a result, the intensity I of light emanating from the analyzer becomes:

$$I\{R+(\Delta R/2)\cos\delta+R\cdot\sin(\Delta\theta+2\phi)\sin\delta\} \qquad (5')$$

This equation, when resolved by a Bessel function, gives:

$$I \sim I(0)+I(p)\sin 2\pi pt+I(2p)\cos 4\pi pt+ \qquad (6)$$

$$I(p)\theta_k, I(2p)\eta_k \qquad (7')$$

What is worthy of notice here is that what p and 2p components represent in this equation is opposite to what the same expressed in equation (7) in "Description of the Prior Art" represent.

The present invention has an above-described constitution and operates in an above-described manner, and combines scanning near field optical microscope with circular polarization modulation thereby to make it possible not only to observe the distribution of optical activities of sample 2 with a high sensitivity and resolution, but also to quantitatively determine the optical rotation and ellipticity of a desired tiny area of the sample. Further, as this method is based on scanning near field optical microscope, it allows the production of a smaller apparatus with a lower cost than is possible with other similar observation means dependent on conventional techniques. The sample 2 may be in the atmosphere, in a liquid, or in a vacuum for measurement, and does not need to be thinly sectioned. Thus, this method does not impose any special restrictions on the preparation of sample.

(2) EXAMPLE 2

Figure 3:
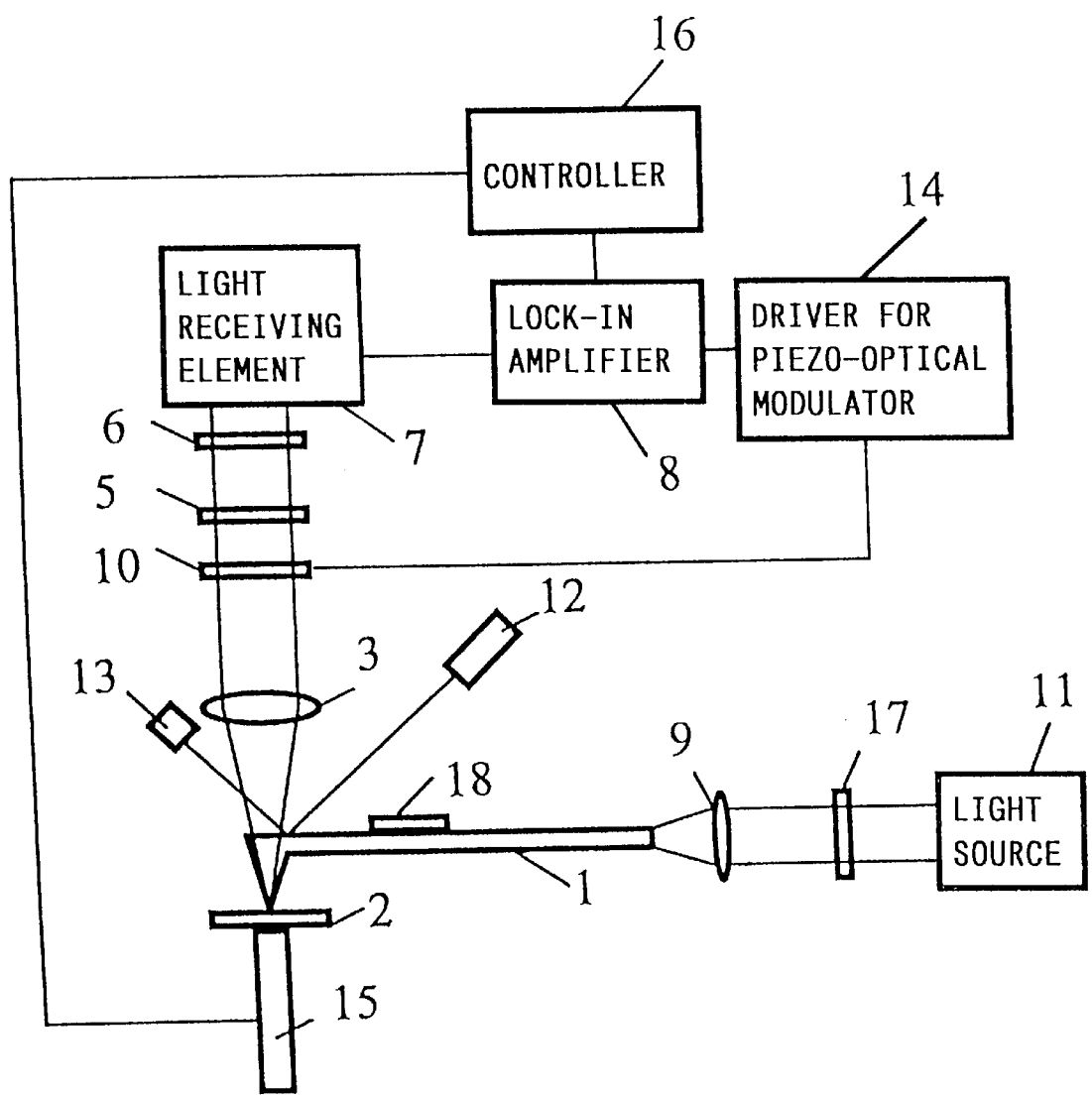
FIG. 3 is an explanatory view showing the constitution of Example 2 of a scanning near field optical microscope based on polarized light according to this invention.

Next, Example 2 according to this invention will be described by means of attached figures. FIG. 3 shows the constitution of Example 2 of this invention. In Example 1 light is passed through a sample for measurement. In this example, measurement is performed using light reflected from a sample. As the basic constitution and operation are the same with those of Example 1, parts achieving the same functions are represented by the same symbols, and their explanation will be omitted.

The fates a beam undergoes, after having emanated from a light source 11, till it exits from the minute opening of optical fiber probe 1 as a minute spot beam are practically the same with those of the beam in Example 1. However, in this example, a piezo-optical modulator 10 is not placed on a light path between the light source 11 and the optical fiber probe 1. As described above, the optical fiber probe 1 often has a property of retarding a beam. This is especially true when the optical fiber probe 1 is bent like a letter L so as to be operable in a dynamic AFM mode because the bent part causes a retardation in a beam. To avoid such inconvenience, a polarization adjusting element 17 is placed on the input side of optical fiber probe 1 and the polarization state of an incident beam is modified by that polarization adjusting element 17 so as to adjust the polarization characteristics of minute spot beam emanating from the minute opening. The polarization adjusting element 17 usually consists of a wavelength plate like a half-wavelength plate or a quarter-wavelength plate, but the use of a compensatory plate will allow a more precise adjustment.

A minute spot beam reflected from the sample 2 after having interacted with the latter is converged by a converging lens 3. The converging lens 2 may be positioned at any place on the light path as long as it efficiently converge the minute spot beam reflected from the sample 2, or it, instead of being made of a lens, may be made of a light-converging mirror like a parabolic mirror, as long as it has a light converging activity. The beam, after being converged by the converging lens 3, is given an optical delay with a frequency of p (Hz) while it passes through a piezo-optical modulator 10, and then passes through an analyzer 5 and filter 6 to be received by a light receiving element 7. As far as only the determination of circular dichroism of a beam from p component is required, the use of analyzer 5 may be omitted. As the remaining constitutions and operations are the same with those of Example 1, description of them will be omitted. Also with this example one can visualize the distribution of optical activities of sample 2 and quantitatively determine those optical activities with a high sensitivity and resolution.

Although in Example 1 the piezo-optical modulator 10 is placed on the input side of optical fiber probe 1, it is needless to say, the device in question may be put between the analyzer 5 and sample 2 as in this example. However, as the piezo-optical modulator 20 usually incorporates an optically active crystal, it is possible to efficiently give an optical delay to an incoming beam by directing the beam to the modulator 20 such that the polarization plane of the beam has a specific angle with respect to the crystal axis. If the piezo-optical modulator 10 is positioned in such a way as to receive light reflected from the sample 2, the polarization plane of the light will not take an optimum angle with respect to the crystal axis, and thus the modulation efficiency and detection sensitivity will often be worsened and lowered.

(3) EXAMPLE 3

Figure 4:
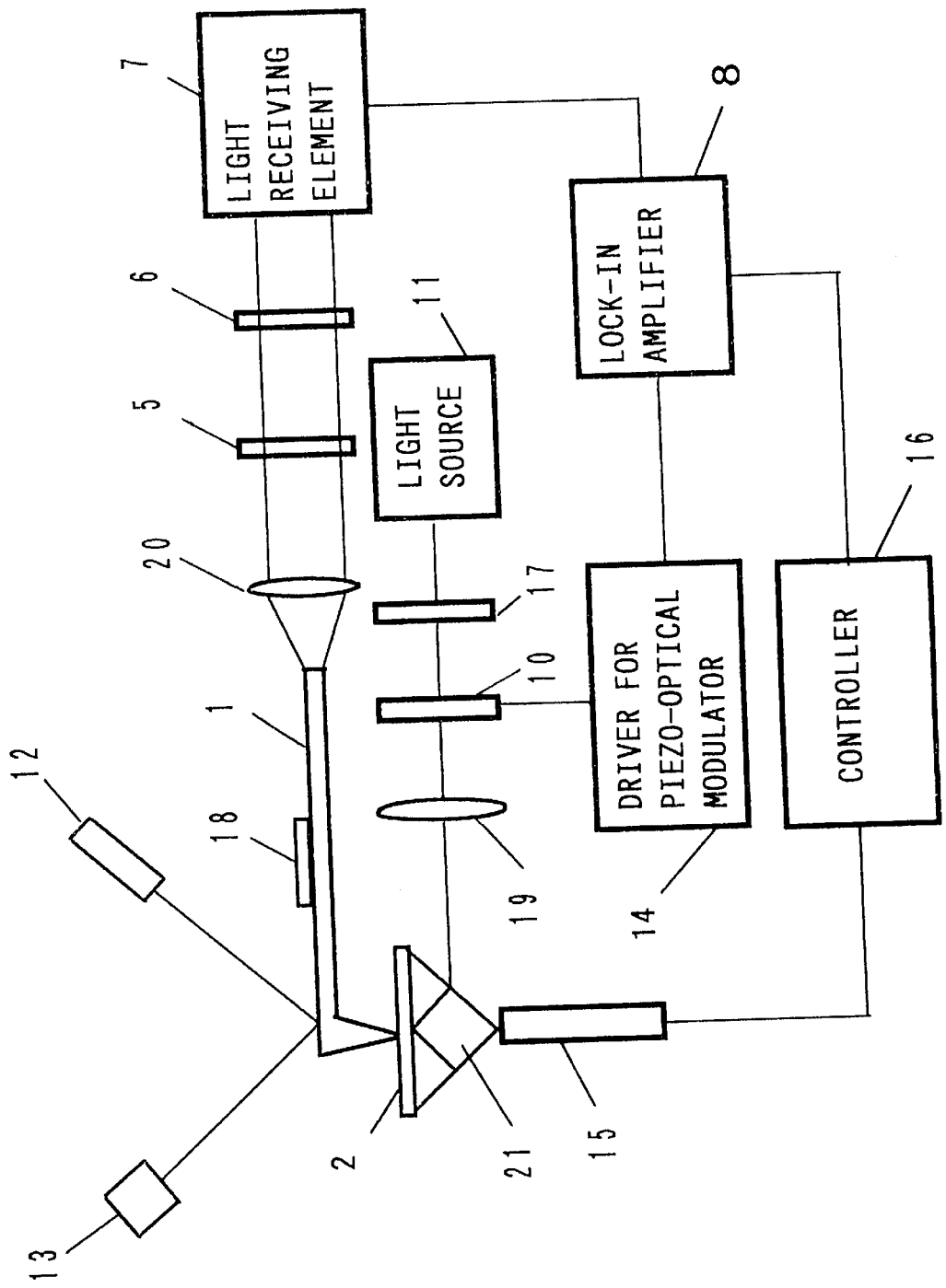
FIG. 4 is an explanatory view showing the constitution of Example 3 of a scanning near field optical microscope based on polarized light according to this invention.

Next, Example 3 according to this invention will be described with reference to attached figures. FIG. 4 represents the constitution of Example 3 of this invention. Although in Examples 1 and 2 an illumination mode is adopted whereby a beam emanating from a minute opening is allowed to illumine a sample, in this example a collection mode is adopted whereby a minute spot beam is detected through a minute opening. Further, a beam is allowed to pass through the sample 2. Parts having the same constitution or achieving the same functions as the corresponding parts of Example 1 are represented by the same symbols, and their explanation will be omitted.

A beam emanating from a light source 11 is given an optical delay during passage through a polarization adjusting element 17 and piezo-optical modulator 10, and this is the same as in Example 1. The beam, after having been given an optical delay, is converged by a converging lens 19 into a convergent beam, and is incident through a side wall onto a triangular prism 2 carrying a sample 2 to be converged to the bottom surface. When the incident angle of the converged beam with respect to the bottom surface of prism exceeds a critical angle, that beam is totally reflected by that bottom surface, and the side of bottom surface facing the sample 2 gives rise to an evanescent beam. When an optical fiber probe having a minute opening at its tip is allowed to approach the sample 2 by the same method as used in Example 1, the evanescent beam present on the surface of sample 2, through interaction with the optical fiber probe 1, is converted into a transmissive beam which enters into the minute opening, transmits through the optical fiber probe 1, and exits from the other end of the same probe. The beam emanating from the other end of probe is collimated by a collimator 20, and is allowed to pass through an analyzer 5 and filter 6 to be received by a light receiving element 7. As the constitution of other elements and their operation are the same with those of Example 1, their explanation will be omitted. With this example, it is also possible to obtain the distribution of optical activities of sample 2 or to quantitatively determine the optical activities thereof with a high sensitivity and resolution.

This example uses the triangular prism 21 in such a way as to totally reflect an incident beam to produce an evanescent beam, but the total reflection may be produced by means of a dark-field illumination and, needless to say, the method is not limited to any specific ones as long as an evanescent beam is produced on the surface of sample 2. It is also needless to say that, as in Example 1, the optical fiber probe 1 is allowed to illumine a tiny area of sample 2, and to receive a beam having undergone an interaction for measurement. In this case, the optical fiber probe must have, at the other end, a beam separating element like a beam splitter which separates a beam into an illumination component and a detection component.

In Examples 1, 2 and 3 described above, the optical fiber probe 1 has a minute opening at its tip, and radiates or transmits a minute spot beam through the minute opening for radiation or for measurement. It is needless to say, however, the probe is not limited to any specific ones as long as it has a light transmitting body acting as a wave guide channel, being made of a comparatively transparent material to the wavelength of beams often used for measurement like quartz or lithium niobate, and has a minute opening at its tip which is equal or less in size than the wavelength of the beam.

In Examples 1, 2 and 3 described above, the piezo-optical modulator 10 is installed, besides the optical fiber probe 1, to give an optical delay. However, many of the above-described light transmitting bodies can give an optical delay through photo-elasticity effects in the presence of an external force. Namely, instead of the piezo-optical modulator 10, a periodic force may be applied to a part of light transmitting body of the probe, and the resulting photo-elasticity effects may be utilized to give an optical delay changing in a periodic manner to a beam during the passage of beam through the light transmitting body. Further, by adjusting the intensity of an external force, it is possible to alter the magnitude of optical delay. As a result, it is possible to reduce the overall size of apparatus.

Further, the method whereby the polarization state of a minute spot beam is adjusted by a polarization adjusting element 17 placed on the input side of a probe consisting of a light transmitting body is effective for the measurement combined not only with the modulation of a circularly polarized beam, but also with a cross-Nichols method. For example, although the optical fiber probe 1 may be bent in a form like a letter L so that the distance between the optical fiber probe 1 and sample 2 may be dynamically changed according to a dynamic AFM mode, the optic fiber probe 1 will then present an optical anisotropy which causes a retardation in a beam passing therethrough. As a result, even if a linearly polarized beam is fed to the optical fiber probe 1, only an elliptically polarized beam will emanate from the minute opening. This inconvenience can be avoided by inserting a polarization adjusting element 17 in such a way as to cancel out the retardation, thereby allowing the minute spot beam to approximate a linearly polarized beam. Therefore, when this arrangement is applied to a cross-Nichols method, the overall detection sensitivity will become higher than is possible with a similar apparatus dependent on the cross-Nichols method which uses an elliptically polarized beam emanating from the minute opening without any special treatment therefor.

In the above-described examples, the polarization adjusting element 17 is installed, besides the optical fiber probe 1, to change the polarization state of a beam before the beam is incident on the optical fiber probe 1. It is needless to say, however, that, when a method is employed which consists of directly applying a force onto part of fiber section of the optical fiber probe 1 and of controlling the intensity of that force, it is possible to alter the polarization state of a beam during its passage through the optical fiber by way of photo-elasticity effects resulting from the external force, and thus to allow the optical fiber probe 1 also to act as a polarization adjusting element 17.

Incidentally, a typical glass material has a photo-elasticity coefficient of about 2–4 ($10^{-6}$·mm$^2$·N–6), and stresses therein cause a retardation in a beam, and hence a beam, when passing through such a glass material, undergoes a change in its polarized state. This can occur in the optical fiber probe 1 of Examples 1, 2 and 3 described above. When the optical fiber (particularly its core section) acting as a light transmitting body is exposed to a vibration externally applied, or falls to vibration of itself having the optical fiber probe fixed, and stresses develop within, a beam passing therethrough has its polarization state altered as a result of photo-elasticity effects, the external vibration acts as a noise source to lower the S/N ratio, or only a slight shift of fixation may destroy the reproducibility of measurements. When the distance between the optical fiber probe 1 and sample 2 is controlled according to a dynamic AFM mode, the optic fiber probe 1 must be bent like a hook as with an AFM cantilever. To take such a form the fiber had to be bent while being heated, and the bent part has residual stresses, and when a beam passes through this part, it receives an optical delay as a result of photo-elasticity effects. This not only applies to a part bent in the form of a hook, but also to the general form of optical fiber probe 1 which is often not symmetrically configured with respect to the axis of light transmission, and results in the development of residual stresses.

To meet above inconvenience, the probe is prepared whose light transmitting body is made of a material having a photo-elasticity coefficient of $1 \times 10^{-6}$ (mm$^2$·N–6) or less. By preparing such a probe it is possible to ignore the effects of stresses caused by external vibrations and fixations, and to suppress the effects of residual stresses developing as a result of asymmetrical configuration with respect to the optical axis to a negligible level. For example, crown glass FK51 or FK52 provided by Shot Co. has a photo-elasticity coefficient of about $0.7-1 \times 10^{-6}$ (mm$^2$·N–6). Further, flint glass SF57 provided by Shot Co. which is composed of quartz containing a large amount of lead oxide has a photo-elasticity coefficient of about $0.02 \times 10^{-6}$ (mm$^2$·N–6), and it can give the same coefficient as small as $0.005 \times 10^{-6}$ (mm$^2$·N–6), depending on the ingredients contained therein. It is also possible to prepare an optical fiber probe from these glass materials. Thus, a light transmitting body made of a material whose photo-elasticity coefficient is $1 \times 10^{-6}$ (mm$^2$·N–6) or less is utilized to form a probe, and with that probe it is possible to make a measurement where changes in polarization characteristics due to external vibrations are effectively suppressed and a satisfactory S/N ratio is maintained. Further, even when the optical fiber probe 1 has its stem bent like a hook as in Examples 1, 2 and 3, it is possible to greatly reduce the changes in polarization state which otherwise a beam would have suffered during passage of the bent part. As is evident from above, preparing a probe from a light transmitting body made of a material having a smaller photo-elasticity coefficient is very useful for a measurement dependent on the use of a polarized beam including a cross-Nichols method as well as circular polarization modulation.

Incidentally, without resorting to the preparation of a probe from a light transmitting body made of a material having a smaller photo-elasticity coefficient, it is possible to suppress the effects of residual stresses which may develop during the preparation of probe, by annealing the light transmitting body thereby to remove residual stresses therein.

(4) EXAMPLE 4

In Examples 1 to 3, the light transmitting body consists of an optical fiber which has its tip sharpened, and has a minute opening on the top of it. However, the method by which to illumine a tiny area of sample by a beam emanating from the tip of probe is not limited to the radiation through a minute opening, but there are a number of variants: an evanescent beam can be produced by plasmon deposited on the surface of a minute ball, or a grating whose lattice pitch is so shortened that the diffraction angle is lost. Further, the method whereby the tip of probe can detect a beam emanating from a tiny area of sample also has a number of variants: an evanescent beam may be produced on the surface of sample by total reflection or by reflection from a surface-coated plasmon.

Besides above a method may be employed whereby a cantilever, instead of a light transmitting body, which is produced after a semiconductor such as silicone or a metal has been sharpened, is utilized as a probe. Then, for example, the surface of sample and the sharpened tip of probe are illuminated by a dark-field illumination as often used in microscopy, to cause a multiple scattering to occur between the sample and cantilever tip, and the scattered beam is measured by an external optical system.

Figure 5:
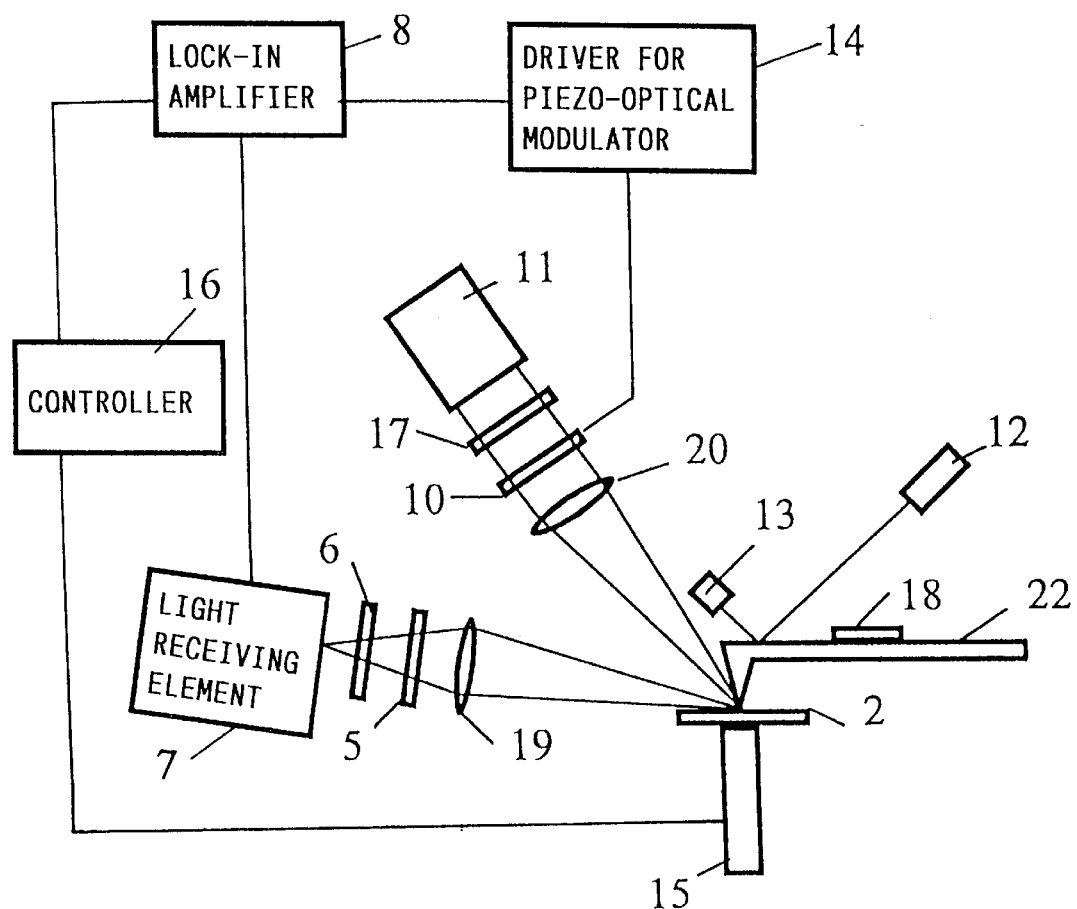
FIG. 5 is an explanatory view showing the constitution of Example 5 of a scanning near field optical microscope based on polarized light according to this invention.

Next, Example 4 of this invention wherein the probe does not consist of a light transmitting body will be described with reference to attached figures. FIG. 5 shows the constitution of Example 4 of this invention. A probe 22 may consist of a metal probe as used in a scanning tunnel microscope or a silicone cantilever as used in a scanning atomic force microscope, or other various materials, but, needless to say, it is not limited to any specific materials as long as the material has a high scattering efficiency. The sharpened tip of probe 22 is allowed to get close to a sample 2. The example depicted in the figure uses an optical lever to move the tip towards the sample, and as this tool is the same as those described earlier, explanation thereof will be omitted. The sample 2 is placed on a piezo actuator 15 and moves in x-, y- and z-axis directions.

A light flux emanating from a light source 11, after having passed through a polarization adjusting element 17 and piezo-optical modulator 10, is converged by a collimator 20 and illumines the sample 2 and the tip of probe 22. This illuminating beam is given a periodically changing optical delay through the piezo-optical modulator 10. The light source 11 usually generates a laser, and there is no element intervened in the light path that may disturb the polarization state of a beam passing along the light path like the optical fiber probe as encountered in foregoing examples, but the polarization adjusting element 17 is used to adjust the polarization direction of an illuminating beam according to the condition of sample 2.

As the tip of probe 22 gets so close to the sample 22 that the distance therebetween is equal to or less than the wavelength of an illuminating beam, a multiple scattering takes place as a result of interaction between the surface of sample 2 and the tip. This multiply scattered beam carries the optical information regarding the surface condition of sample 2 depending on the size of tip of the probe 22. A converging lens converges this scattered beam which is then passed through an analyzer 5 and filter 6 to be received by a light receiving element 7. As the subsequent processes are the same as those of foregoing examples, explanation thereof will be omitted. Adjusting the angles of light source 11 and of light receiving element 7 with respect to the sample 2 so that a beam emanating from the light source 11 to illumine the sample 2 and probe 22 may no enter the light receiving element, will enable a selective pick-up of a multiply scattered beam, and achievement of a measurement with a satisfactory S/N ratio. As is evident from above, even if a probe does not consist of a light transmitting body, it is possible to constitute a scanning near field optical microscope based on circular polarization modulation, and to observe optical activities of a sample with a high sensitivity.

When a beam from the light source 11 radiates from one direction onto the sample 2 as in FIG. 5, it is needless to say that entry of the radiating beam from the light source 11 into the light receiving element 7 should be avoided as much as possible. Further, this example is based on a transmission type apparatus, but, needless to say, what is mentioned above also applies to a reflection type apparatus.

Examples 1 to 4 described above use an optical lever to detect the displacement of optical fiber probe 1 or probe 22. However, needless to say, the method is not limited to an optical lever or any other specific methods, as long as the method permits detection of the minute displacement of optical fiber probe 1 or probe 22. For example, when a dynamic AFM mode is employed, the probe may be applied on a quartz vibration detector, and the changes in vibration of probe be followed after voltages delivered from the quartz vibration detector have been monitored.

In Examples 1 to 4 described above, the method by which to control the distance between the optical fiber probe 1 or probe 22 and the sample 2 is based on a dynamic AFM mode. However, needless to say, the method is not limited to any specific modes, as long as the distance between the optical fiber probe 1 or probe 22 and the sample 2 can be rendered to any small size at will: the distance in question may be adjusted according to a static AFM mode, or by light interference, or on the basis of a shearing force produced as a result of interaction between the two elements here concerned, or through the utilization of a tunnel current. If the latter method is used, the optical fiber probe 1 or probe 22 may not be bent like a letter L.

Although, in Examples 1 to 4 described above, the distance between the optical fiber probe 1 or probe 22 and the sample 2 is measured and actively controlled on the basis of the measurement, the method is not limited to this. For example, the probe and sample are allowed to move relative to each other to cause a current to flow therebetween, thereby maintaining constant the distance between the probe and sample surface by virtue of the viscosity of fluid as in a hard disk drive where the magnetic head floats by a certain definite amount (e.g., about 100 nm) over the disk by virtue of an air bearing. Thus, needless to say, the method does not require necessarily measurement of the distance between the probe and sample surface and a continuous monitoring of the proximity of the two elements here concerned, but any method, as long as it allows the probe and sample surface to be close and constant to each other, can be used with the same profit.

In Examples 1 to 4 described above, the light source 11 generates a laser composed of a beam of a single wavelength. However, a Xenon lamp may be used as the light source 11, and light therefrom may be used after it has passed through a spectroscope so that an appropriate component might be selected. In this case, measurement can be performed using beams with different wavelengths.

What is claimed is:

1. A scanning near field optical microscope based on the use of polarized light wherein the interval between the tip of a probe and the surface of a sample or a medium to be measured is kept so small as to be within an action distance where an inter-atomic force or other interactive forces result between the tip and the surface, a beam is scanned over the surface through a means allowing a two-dimensional scanning, the beam is radiated onto a tiny area of the surface or the beam emanating from a tiny area of the surface is detected, and therewith the form of sample and two-dimensional optical information thereof are simultaneously obtained, comprising:

a light source;

a probe with a sharpened tip;

a means to maintain the interval between the tip and the surface within an action distance where an inter-atomic force or other interactive forces result between the tip and the surface;

a means to obtain a polarized beam carrying the optical information of a tiny area of sample or medium, by allowing a beam from the light source to interact with the surface at the tip;

a light receiving means to receive the polarized beam;

a modulating means which is placed on the light path between the light source and light receiving means and gives a periodically changing optical delay to the beam; and a rectifying means to selectively separate, out of the output from the light receiving means, wave components having frequencies integer times as high as the modulation frequency worked by the modulating means.

2. A scanning near field optical microscope based on the use of polarized light as claimed in claim 1, the probe has a light transmitting body.

3. A scanning near field optical microscope based on the use of polarized light as claimed in claim 2, wherein the modulating means placed on the light path between the light source and light receiving means to give a periodically changing optical delay to a beam further comprising a means to impose a periodically changing stress to the light transmitting body.

4. A scanning near field optical microscope based on the use of polarized light as claimed in claim 1 wherein the means to maintain the interval between the tip and the surface within an action distance where an inter-atomic force or other interactive forces result between the tip and the surface, comprising:

a moving means to alter the distance between the tip and the surface;

a distance determining means to determine the distance between the tip and the surface; and a control means to maintain constant the distance between the tip and the surface on the basis of a signal delivered by the distance determining means.

5. A scanning near field optical microscope based on the use of polarized light as claimed in claim 4, wherein the distance determining means comprising:

a vibrating means to vibrate the tip and the surface relative to each other in a horizontal or vertical direction; and a displacement detecting means to detect the displacement of the tip.

6. A scanning near field optical microscope based on the use of polarized light wherein the interval between the tip of a probe and the surface of a sample or a medium to be measured is kept so small as to be within an action distance where an inter-atomic force or other interactive forces result between the tip and the surface, a beam is scanned over the surface through a means allowing a two-dimensional scanning, the beam is radiated onto a tiny area of the surface or the beam emanating from a tiny area of the surface is detected, and therewith the form of sample and two-dimensional optical information thereof are simultaneously obtained, comprising:

a light source;

a probe with a sharpened tip and a light transmitting body;

a means to maintain the interval between the tip and the surface within an action distance where an inter-atomic force or other interactive forces result between the tip and the surface;

a means to obtain a polarized beam carrying the optical information of a tiny area of sample or medium, by allowing a beam from the light source to interact with the surface at the tip; and a light receiving means to receive the polarized beam, and wherein a material constituting the light transmitting body has a photo-elasticity coefficient of $1.0 \times 10^{-6}$ [$mm^2 \cdot N-1$] or less.

7. A scanning near field optical microscope based on the use of polarized light as claimed in claim 6, wherein the material constituting the light transmitting body is quartz glass containing lead oxide.

8. A scanning near field optical microscope based on the use of polarized light wherein the interval between the tip of a probe and the surface of a sample or a medium to be measured is kept so small as to be within an action distance where an inter-atomic force or other interactive forces result between the tip and the surface, a beam is scanned over the surface through a means allowing a two-dimensional scanning, the beam is radiated onto a tiny area of the surface or the beam emanating from a tiny area of the surface is detected, and therewith the form of sample and two-dimensional optical information thereof are simultaneously obtained, comprising:

a light source;

a probe with a sharpened tip and a light transmitting body;

a means to maintain the interval between the tip and the surface within an action distance where an inter-atomic force or other interactive forces result between the tip and the surface;

a means to obtain a polarized beam carrying the optical information of a tiny area of sample or medium, by allowing a beam from the light source to interact with the surface at the tip;

a light receiving means to receive the polarized beam; and a means to confer an optical delay by causing a stress in the light transmitting body.

* * * * *